(12) United States Patent
Merkel et al.

(10) Patent No.: US 8,519,200 B1
(45) Date of Patent: Aug. 27, 2013

(54) AZEOTROPIC COMPOSITIONS OF 1,1,3,3-TETRACHLORO-1-FLUOROPROPANE AND HYDROGEN FLUORIDE

(75) Inventors: Daniel C. Merkel, West Seneca, NY (US); Konstantin A. Pokrovski, Orchard Park, NY (US); Hang T. Pham, Amherst, NY (US); Hsueh Sung Tung, Getzville, NY (US); Ryan Hulse, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/403,011

(22) Filed: Feb. 23, 2012

(51) Int. Cl.
| | |
|---|---|
| C07C 17/07 | (2006.01) |
| C07C 17/087 | (2006.01) |
| C07C 17/38 | (2006.01) |
| B01F 1/00 | (2006.01) |
| C09K 3/00 | (2006.01) |
| C09K 5/04 | (2006.01) |
| C09K 3/30 | (2006.01) |
| C11D 17/00 | (2006.01) |

(52) U.S. Cl.
USPC ........... 570/164; 570/124; 570/170; 252/2; 252/71; 252/182.12; 510/177; 510/408; 510/412

(58) Field of Classification Search
USPC .......... 570/124, 164, 170; 252/2, 71, 182.12; 510/177, 408, 412
See application file for complete search history.

(56) References Cited

U.S. PATENT DOCUMENTS

| | | | | |
|---|---|---|---|---|
| 5,763,706 | A | * | 6/1998 | Tung et al. ................. 570/167 |
| 5,777,184 | A | * | 7/1998 | Van Der Puy et al. ........ 570/135 |
| 6,316,682 | B1 | * | 11/2001 | Nakada et al. ................ 570/170 |
| 6,660,893 | B2 | | 12/2003 | Ewing et al. |
| 6,844,475 | B1 | * | 1/2005 | Tung et al. ................. 570/168 |
| 7,371,363 | B2 | | 5/2008 | Merkel et al. |
| 2007/0129580 | A1 | * | 6/2007 | Mukhopadhyay et al. ... 570/155 |
| 2010/0048961 | A1 | | 2/2010 | Merkel et al. |
| 2011/0201853 | A1 | | 8/2011 | Tung et al. |
| 2012/0059199 | A1 | * | 3/2012 | Pokrovski et al. ........... 570/155 |
| 2012/0059200 | A1 | * | 3/2012 | Pokrovski et al. ........... 570/156 |
| 2012/0178977 | A1 | * | 7/2012 | Merkel et al. ................ 570/153 |
| 2012/0296127 | A1 | * | 11/2012 | Cottrell et al. ............... 570/135 |
| 2013/0035526 | A1 | * | 2/2013 | Elsheikh et al. ............. 570/156 |
| 2013/0041190 | A1 | * | 2/2013 | Pigamo et al. .............. 570/156 |

OTHER PUBLICATIONS

Kim et al.; (Mar. 1996) "A Study to Determine the Existence of an Azeotropic R-22 "Drop-In" Substitute"; Source: Report from the Building Environment Division of the Building & Fire Research Laboratory of the U.S. Department of Commerce.
G. Morrison & M.O. Mclinden; (1993) "Azeotropy in refrigerant mixtures"; Source: International Journal of Refrigeration, vol. 16, No. 2, pp. 129-138.

* cited by examiner

Primary Examiner — Joseph D Anthony
(74) Attorney, Agent, or Firm — Bruce O. Bradford

(57) ABSTRACT

Provided are azeotropic or azeotrope-like mixtures of 1,1,3,3-tetrachloro-1-fluoropropane (HCFC-241fa) and hydrogen fluoride. Such compositions are useful as an intermediate in the production of HFC-245fa and HCFO-1233zd.

20 Claims, 1 Drawing Sheet

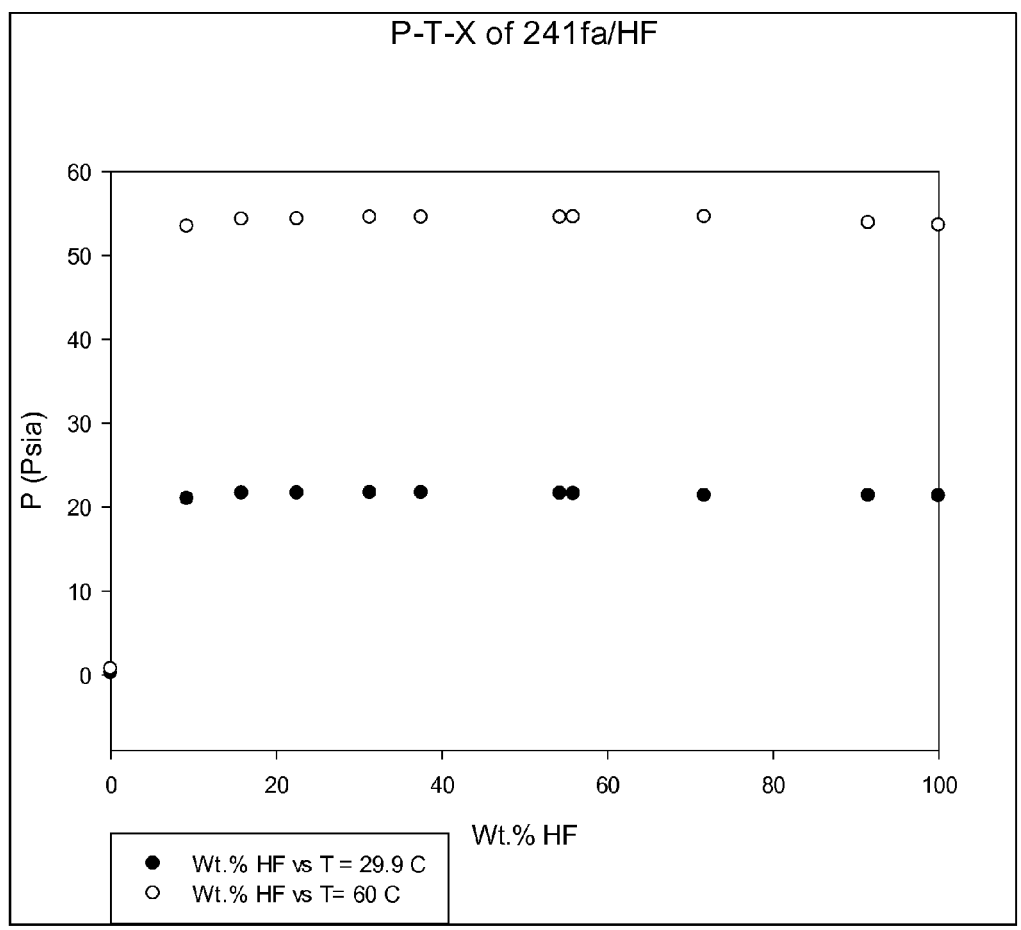

US 8,519,200 B1

AZEOTROPIC COMPOSITIONS OF 1,1,3,3-TETRACHLORO-1-FLUOROPROPANE AND HYDROGEN FLUORIDE

FIELD OF THE INVENTION

The present invention pertains to azeotropic or azeotrope-like compositions of 1,1,3,3-tetrachloro-1-fluoropropane (HCFC-241fa or 241fa) and hydrogen fluoride (HF).

BACKGROUND OF THE INVENTION

Chlorofluorocarbon (CFC) based chemicals have been widely use in industry in a variety of different applications including as refrigerants, aerosol propellants, blowing agents and solvents, among others. However, certain CFCs are suspected of depleting the Earth's ozone layer. Accordingly, more environmentally friendly substitutes have been introduced as replacements for CFCs. For example, 1,1,1,3,3-pentafluoropropane (HFC-245fa) is recognized as having favorable physical properties for certain industrial applications, such as foam blowing agents and solvents, and therefore is consider to be a good substitute for the CFCs previously used for these applications. Unfortunately, the use of certain hydrofluorocarbons, including HFC-245fa, in industrial applications is now believed to contribute to the global warming. Accordingly, more environmentally friendly substitutes for hydrofluorocarbons are now being sought.

The compound 1-chloro-3,3,3-trifluoropropene, also known as HCFO-1233zd or simply 1233zd, is a candidate for replacing HFC-245fa in some applications, including uses as blowing agents and solvents. 1233zd has a Z-isomer and an E-isomer. Due to differences in the physical properties between these two isomers, pure 1233zd (E), pure 1233zd (Z), or certain mixtures of the two isomers may be suitable for particular applications as refrigerants, propellants, blowing agents, solvents, or for other uses.

1,1,3,3-Tetrachloro-1-fluoropropane (HCFC-241fa) is a reactant used in the production of both 245fa and 1233zd. See for example U.S. Pat. Nos. 5,763,706 and 6,844,475. See also, U.S. Patent Publication No. 2011-0201853 which is directed to an integrated process and methods of producing 1233zd (E).

It has now been found that an important intermediate in the production of both 245fa and 1233zd, is an azeotrope or azeotrope-like mixture of 1,1,3,3-tetrachloro-1-fluoropropane (HCFC-241fa) and hydrogen fluoride (HF). This intermediate, once formed, may thereafter be separated into its component parts, for example by extraction or distillation techniques. HCFC-241fa has a boiling point of about 140.2° C. and HF has a boiling point of about 20° C. at standard atmospheric pressure. These azeotropic or azeotrope-like compositions find use not only as reactor feeds in the production of 245fa and 1233zd, but they are additionally useful as solvent compositions for removing surface oxidation from metals.

SUMMARY OF THE INVENTION

The present invention is directed to azeotropic or azeotrope-like mixtures of 1,1,3,3-tetrachloro-1-fluoropropane (HCFC-241fa) and hydrogen fluoride. Such compositions are useful as an intermediate in the production of HFC-245fa and HCFO-1233zd.

In certain embodiments of this mixture, the composition comprises effective amounts of 1,1,3,3-tetrachloro-1-fluoropropane (HCFC-241fa) and hydrogen fluoride.

In certain embodiments of this mixture, the composition comprises from about 99 to about 1 weight percent HF.

In certain embodiments of this mixture, the composition comprises from about 70 weight percent to about 99 weight percent HF.

In certain embodiments of this mixture, the composition comprises from about 70 weight percent to about 99 weight percent HF.

In certain embodiments of this mixture, the composition comprises from about 1 to about 99 weight percent HCFC-241fa.

In certain embodiments of this mixture, the composition comprises from about 70 weight percent to about 1 weight percent HCFC-241fa.

In certain embodiments of this mixture, the composition comprises from about 30 weight percent to about 1 weight percent HCFC-241fa.

In certain embodiments of this mixture, the composition has a boiling point of about from 21° C. to about 60° C. at a pressure from about 16.5 psia to about 54.6 psia.

In another aspect of the invention there is provided a heterogeneous azeotropic composition consisting essentially of 1,1,3,3-tetrachloro-1-fluoropropane (HCFC-241fa) and hydrogen fluoride (HF).

In certain embodiments of this mixture, the composition consists essentially of from about 90 to about 99 weight percent hydrogen fluoride and from about 10 to about 1 weight percent 1,1,3,3-tetrachloro-1-fluoropropane (HCFC-241fa), which composition has a boiling point of about 30° C. to about 60° C. at pressure of about 21.4 psia to pressure of about 53.9 psia.

Another aspect of the present invention is directed to a method of forming a heterogeneous azeotropic or azeotrope-like composition comprising the step of blending components which consist essentially of from about 1 to about 99 weight percent hydrogen fluoride and from about 99 to about 1 weight percent 1,1,3,3-tetrachloro-1-fluoropropane (HCFC-241fa), which composition has a boiling point of about from 21° C. to about 60° C. at pressure of about from 16.5 psia to about 54.6 psia.

In certain embodiments of this method, the composition consists of hydrogen fluoride and 1,1,3,3-tetrachloro-1-fluoropropane (HCFC-241fa).

In certain embodiments of this method, the composition comprises from about 99 to about 1 weight percent HF.

In certain embodiments of this method, the composition comprises from about 70 weight percent to about 99 weight percent HF.

In certain embodiments of this method, the composition comprises from about 70 weight percent to about 99 weight percent HF.

In certain embodiments of this method, the composition comprises from about 1 to about 99 weight percent HCFC-241fa.

In certain embodiments of this method, the composition comprises from about 70 weight percent to about 1 weight percent HCFC-241fa.

In certain embodiments of this method, the composition comprises from about 30 weight percent to about 1 weight percent HCFC-241fa.

In certain embodiments of this method, the composition has a boiling point of about from 21° C. to about 60° C. at a pressure from about 16.5 psia to about 54.6 psia.

In certain embodiments of this method, the composition consists of about 98±2 weight percent HF and about 2±2 weight percent HCFC-241fa, and has a boiling point of about 21° C. at 16.5 psia.

Another aspect of the present invention is directed to a method of separating 241fa from the azeotropic like mixture of 241fa and HF comprising the step of extracting the HF from the mixture.

In certain embodiments of this method, the extraction of HF is accomplished using water or other aqueous solution.

In certain embodiments of this method, the extraction of HF is accomplished using sulfuric acid.

In certain embodiments of this method, the extraction of HF is accomplished by distillation.

In certain embodiments of this method, the distillation comprises extractive distillation.

In certain embodiments of this method, the distillation comprises pressure swing distillation.

BRIEF DESCRIPTION OF THE DRAWING

FIG. 1 shows a plot of the vapor pressures of the mixtures formed in Example 1 as measured at 30° C. and 60° C.

DETAILED DESCRIPTION OF THE INVENTION

When 1,1,3,3-tetrachloro-1-fluoropropane (HCFC-241fa) and HF were fed to a reactor, it was found that the HCFC-241fa forms an azeotropic or azeotrope-like mixture with HF. The unreacted HCFC-241fa/HF intermediate was found in the product stream.

The thermodynamic state of a fluid is defined by its pressure, temperature, liquid composition and vapor composition. For a true azeotropic composition, the liquid composition and vapor phase are essentially equal at a given temperature and pressure. In practical terms this means that the components cannot be separated during a phase change. For the purpose of this invention, an azeotrope is a liquid mixture that exhibits a maximum or minimum boiling point relative to the boiling points of surrounding mixture compositions.

An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling.

For the purpose of this invention, azeotropic compositions are defined to include azeotrope-like compositions, which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of hydrogen fluoride and HCFC-241fa to form an azeotropic or azeotrope-like composition. By effective amount is meant an amount of each component which, when combined with the other component, results in the formation of an azeotrope or azeotrope-like mixture. The inventive compositions preferably are binary azeotropes which consist essentially of combinations of only hydrogen fluoride with HCFC-241fa.

In the preferred embodiment, the inventive composition contains from about 99 to about 1 weight percent HF, preferably from about 70 weight percent to about 99 weight percent and most preferably from about 70 weight percent to about 99 weight percent. In the preferred embodiment, the inventive composition contains from about 1 to about 99 weight percent HCFC-241fa preferably from about 70 weight percent to about 1 weight percent and most preferably from about 30 weight percent to about 1 weight percent. The composition of the present invention has a boiling point of about from 21° C. to about 60° C. at a pressure from about 16.5 psia to about 54.6 psia. An azeotropic or azeotrope-like composition having about 98±2 weight percent HF and about 2±2 weight percent HCFC-241fa has been found to boil at about 21° C. and 16.5 psia.

The following non-limiting examples serve to illustrate the invention.

Example 1

15.4 g of 1,1,3,3-tetrachloro-1-fluoropropane (HCFC-241fa) were dissolved in 12.9 g of HF to form a heterogeneous azeotrope mixture. This experiment was done at 21° C., and at 16.5 psia.

Example 2

Binary compositions containing solely 1,1,3,3-tetrachloro-1-fluoropropane (HCFC-241fa) and HF are blended to form a heterogeneous azeotrope mixtures at different compositions. The vapor pressures of the mixtures are measured at about 29.9° C. and 60° C. and the following results are noticed.

Table 1 shows the vapor pressure measurement of HCFC-241fa and HF as a function of composition of weight percent HF at constant temperatures of about 29.9° C. and 60° C.

TABLE 1

| P-T-X of HCFC-241fa/HF System | | |
|---|---|---|
| Wt. % HF | T = 29.9° C. | T = 60° C. |
| 0.0 | 0.23 | 0.72 |
| 9.2 | 21.00 | 53.44 |
| 15.8 | 21.64 | 54.29 |
| 22.5 | 21.67 | 54.32 |
| 31.3 | 21.69 | 54.50 |
| 37.5 | 21.68 | 54.50 |
| 54.3 | 21.62 | 54.50 |
| 55.9 | 21.58 | 54.55 |
| 71.7 | 21.35 | 54.56 |
| 91.5 | 21.36 | 53.87 |
| 100.0 | 21.34 | 53.58 |

These data also show that the mixture is an azeotrope since the vapor pressures of mixtures of HCFC-241fa and HF are higher, at all indicated blend proportions, than HCFC-241fa and HF alone, i.e., as indicated in the first and last rows when HF is 0.0 wt % and HCFC-241fa is at 100.0 wt % as well as when HCFC-241fa is at 0.0 wt % and HF is at 100.0 wt. %. The data from Table 1 are shown in graphic form in FIG. 1.

Example 3

The azeotropic composition of the HCFC-241fa/HF mixture is also verified by Vapor-Liquid—Liquid Equilibrium (VLLE) experiment. 57.5 g of 1,1,3,3-tetrachloro-1-fluoropropane (HCFC-241fa) are dissolved in 32.5 g of HF to form a heterogeneous mixture (visual observation) at 21° C. The vapor compositions of the mixture were sampled at room temperature of 21° C. The result shows that the azeotropic composition is about 98±2 wt % HF at 21° C.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An azeotropic composition consisting essentially of effective amounts of 1,1,3,3-tetrachloro-1-fluoropropane (HCFC-241fa) and hydrogen fluoride (HF).

2. The composition of claim 1, wherein the composition comprises from about 99 to about 1 weight percent HF.

3. The composition of claim 1, wherein the composition comprises from about 70 to about 99 weight percent HF.

4. The composition of claim 1, wherein the composition comprises from about 1 to about 99 weight percent HCFC-241fa.

5. The composition of claim 1, wherein the composition comprises from about 70 weight percent to about 1 weight percent HCFC-241fa.

6. The composition of claim 1, wherein the composition comprises from about 30 weight percent to about 1 weight percent HCFC-241fa.

7. The composition of claim 1, wherein the composition has a boiling point of about from 21° C. to about 60° C. at a pressure from about 16.5 psia to about 54.6 psia.

8. An azeotropic or azeotrope-like composition which includes about 98±2 weight percent HF and about 2±2 weight percent HCFC-241fa and has a boiling point of about 21° C. at 16.5 psia.

9. An azeotropic or azeotrope-like composition which consists essentially of from about 90 to about 99 weight percent hydrogen fluoride and from about 10 to about 1 weight percent 1,1,3,3-tetrachloro-1-fluoropropane (HCFC-241fa), which composition has a boiling point of about 30° C. to about 60° C. at pressure of about 21.4 psia to pressure of about 53.9 psia.

10. The composition of claim 9, which consists of hydrogen fluoride and 1,1,3,3-tetrachloro-1-fluoropropane (HCFC-241fa).

11. A method of forming a heterogeneous azeotropic or azeotrope-like composition comprising the step of blending components which consist essentially of from about 1 to about 99 weight percent hydrogen fluoride and from about 99 to about 1 weight percent 1,1,3,3-tetrachloro-1-fluoropropane (HCFC-241fa), which composition has a boiling point of about from 21° C. to about 60° C. at pressure of about from 16.5 psia to about 54.6 psia.

12. The method of claim 11, wherein the composition consists of hydrogen fluoride and 1,1,3,3-tetrachloro-1-fluoropropane (HCFC-241fa).

13. The method of claim 11, wherein the composition comprises from about 99 to about 1 weight percent HF.

14. The method of claim 11, wherein the composition comprises from about 70 weight percent to about 99 weight percent HF.

15. The method of claim 11, wherein the composition comprises from about 70 weight percent to about 99 weight percent HF.

16. The method of claim 11, wherein the composition comprises from about 1 to about 99 weight percent HCFC-241fa.

17. The method of claim 11, wherein the composition comprises from about 70 weight percent to about 1 weight percent HCFC-241fa.

18. The method of claim 11, wherein the composition comprises from about 30 weight percent to about 1 weight percent HCFC-241fa.

19. The method of claim 11, wherein the composition has a boiling point of about from 21° C. to about 60° C. at a pressure from about 16.5 psia to about 54.6 psia.

20. The method of claim 11, wherein the composition consists of about 98±2 weight percent HF and about 2±2 weight percent HCFC-241fa, and has a boiling point of about 21° C. at 16.5 psia.

* * * * *